US012392755B2

(12) United States Patent
Takemoto

(10) Patent No.: US 12,392,755 B2
(45) Date of Patent: Aug. 19, 2025

(54) QUALITY DETERMINATION SYSTEM OF JELLY FOR SWALLOWING AND QUALITY DETERMINATION METHOD OF JELLY FOR SWALLOWING

(71) Applicant: FUJIFILM Corporation, Tokyo (JP)

(72) Inventor: Kosei Takemoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 377 days.

(21) Appl. No.: 18/307,543

(22) Filed: Apr. 26, 2023

(65) Prior Publication Data

US 2023/0258610 A1 Aug. 17, 2023

Related U.S. Application Data

(63) Continuation of application No. PCT/JP2021/036747, filed on Oct. 5, 2021.

(30) Foreign Application Priority Data

Nov. 30, 2020 (JP) .................................. 2020-198806

(51) Int. Cl.
*G01N 29/44* (2006.01)
*A61B 8/08* (2006.01)
(Continued)

(52) U.S. Cl.
CPC ....... *G01N 29/4409* (2013.01); *A61B 8/0833* (2013.01); *G01N 29/02* (2013.01); *G01N 29/06* (2013.01)

(58) Field of Classification Search
CPC .... G01N 29/4409; G01N 29/02; G01N 29/06; A61B 8/0833; A61B 8/4427; A61B 8/4472; A61B 8/5223
See application file for complete search history.

(56) References Cited

U.S. PATENT DOCUMENTS

2002/0116987 A1* 8/2002 Braithwaite ............. G01N 3/08
73/54.01

FOREIGN PATENT DOCUMENTS

JP H0718843 * 1/1987
JP S63-186141 A 8/1988
(Continued)

OTHER PUBLICATIONS

International Search Report issued in PCT/JP2021/036747; mailed Dec. 14, 2021.
(Continued)

*Primary Examiner* — Tarun Sinha
(74) *Attorney, Agent, or Firm* — Studebaker Brackett PLLC

(57) ABSTRACT

A quality determination system of a jelly for swallowing and a quality determination method of a jelly for swallowing that can non-invasively determine quality of a jelly for swallowing based on an ultrasound image are provided. A quality determination system of a jelly for swallowing includes an ultrasound probe, an image generation unit that generates an ultrasound image from a reception signal obtained by transmitting and receiving an ultrasound beam to and from a subject using the ultrasound probe, an image analysis unit that acquires a first air bubble pattern in a jelly for swallowing by analyzing the ultrasound image generated in a state where the ultrasound probe is in contact with an outer surface of an unopened package in which the jelly for swallowing including air bubbles is sealed, and a quality determination unit that determines quality of the jelly for swallowing based on the first air bubble pattern.

20 Claims, 9 Drawing Sheets

(51) Int. Cl.
    *G01N 29/02*     (2006.01)
    *G01N 29/06*     (2006.01)

(56) References Cited

FOREIGN PATENT DOCUMENTS

| JP | H10214758 | * | 8/1989 |
|---|---|---|---|
| JP | 2001-218769 A | | 8/2001 |
| JP | 2012-147757 A | | 8/2012 |
| JP | 2019-104733 A | | 6/2019 |
| WO | 2013/187283 A1 | | 12/2013 |
| WO | 2018/207935 A1 | | 11/2018 |

OTHER PUBLICATIONS

International Preliminary Report on Patentability (Chapter I) and Written Opinion of the International Searching Authority issued in PCT/JP2021/036747; issued May 30, 2023.

* cited by examiner

QUALITY DETERMINATION SYSTEM OF JELLY FOR SWALLOWING AND QUALITY DETERMINATION METHOD OF JELLY FOR SWALLOWING

CROSS-REFERENCE TO RELATED APPLICATIONS

This application is a Continuation of PCT International Application No. PCT/JP2021/036747 filed on Oct. 5, 2021, which claims priority under 35 U.S.C. § 119(a) to Japanese Patent Application No. 2020-198806 filed on Nov. 30, 2020. The above applications are hereby expressly incorporated by reference, in their entirety, into the present application.

BACKGROUND OF THE INVENTION

1. Field of the Invention

The present invention relates to a quality determination system of a jelly for swallowing and a quality determination method of a jelly for swallowing used in a case of examining dysphagia.

2. Description of the Related Art

As a method of examining dysphagia in ingestion of an elderly person, a possibility of non-invasively examining dysphagia using an ultrasound wave has been reviewed. In a case of examining dysphagia using an ultrasound wave, a subject is asked to swallow food for examination, and an ultrasound image of a pharynx part of the subject in swallowing is observed to evaluate presence or absence of dysphagia in the subject, for example, presence or absence of a residue of the food for examination in the pharynx part of the subject and presence or absence of aspiration.

Here, for example, JP2012-147757A, WO2013/187283A, and JP1988-186141A (JP-S63-186141A) are prior art literature as a reference for the present invention.

JP2012-147757A discloses an ultrasound tomography imaging aid agent obtained by cooling aerated molten gel-like food to a gel.

WO2013/187283A discloses a jelly-like semisolid examination material in which a microbubble suspension for examining an ingestion and swallowing function using an ultrasound examination method is added.

JP1988-186141A (JP-S63-186141A) discloses emission of an ultrasound wave and reception of a reflected wave by causing an ultrasound probe to abut on one outer surface of a package filled with contents such as liquid food, and determination of presence or absence of a change in quality of the contents and of a degree of the change in quality based on a detection value.

SUMMARY OF THE INVENTION

In JP2012-147757A and in WO2013/187283A, while a jelly for swallowing is disclosed as food for examination in a case of examining dysphagia using an ultrasound wave, determination of quality of the jelly for swallowing is not disclosed.

In JP1988-186141A (JP-S63-186141A), while the determination of the presence or absence of the change in quality of the contents with which the package is filled and of the degree of the change in quality using an ultrasound wave is disclosed, this determination is performed based on at least one of a difference between sound speeds of the emitted wave and the received wave or the sound speed of the received wave, a time from the emission to the reception, or a degree of attenuation of ultrasound energy. Determination based on an ultrasound image is not disclosed.

Here, because of a principle of examination using an ultrasound wave, it is difficult to recognize the residue of the jelly for swallowing as an ultrasound image.

According to the research of the present inventor, it has been found that the residue of the jelly for swallowing in the ultrasound image is easily detected by sealing granular air bubbles in the jelly for swallowing to facilitate reflection of the ultrasound wave. In addition, according to the research of the present inventor, it is clear that a shape of an air bubble pattern sealed in the jelly for swallowing changes because of a change over time, a change in temperature of a storage location, and the like.

In a case where the change in the shape of the air bubble pattern is reflected on the ultrasound image, evaluation of the residue of the jelly for swallowing by a user, detection performance of a machine learning model for the residue of the jelly for swallowing, and the like may be adversely affected. Accordingly, the quality of the jelly for swallowing needs to be determined before examination of dysphagia.

An object of the present invention is to provide a quality determination system of a jelly for swallowing and a quality determination method of a jelly for swallowing that can non-invasively determine quality of a jelly for swallowing based on an ultrasound image.

In order to achieve the above object, according to an aspect of the present invention, there is provided a quality determination system of a jelly for swallowing, the system comprising an ultrasound probe, an image generation unit that generates an ultrasound image from a reception signal obtained by transmitting and receiving an ultrasound beam to and from a subject using the ultrasound probe, an image analysis unit that acquires a first air bubble pattern in a jelly for swallowing by analyzing the ultrasound image generated in a state where the ultrasound probe is in contact with an outer surface of an unopened package in which the jelly for swallowing including air bubbles is sealed, and a quality determination unit that determines quality of the jelly for swallowing based on the first air bubble pattern.

Here, it is preferable that the quality determination unit detects a change in a shape of the first air bubble pattern with respect to an air bubble pattern in the jelly for swallowing in sealing the jelly for swallowing in the package and determines the quality of the jelly for swallowing based on the change in the shape of the first air bubble pattern.

In addition, it is preferable that the quality determination system of a jelly for swallowing further comprises a memory in which a plurality of reference ultrasound images in which the air bubble pattern has sequentially changed in accordance with deterioration of the quality of the jelly for swallowing are stored, in which the quality determination unit detects the change in the shape of the first air bubble pattern by comparing the ultrasound image with the plurality of reference ultrasound images stored in the memory.

In addition, it is preferable that the quality determination unit includes a machine learning model that takes the first air bubble pattern as an input and that outputs an estimation result obtained by estimating the quality of the jelly for swallowing, and determines the quality of the jelly for swallowing based on the estimation result.

In addition, it is preferable that the quality determination system of a jelly for swallowing further comprises an optical image acquisition unit that acquires an optical image of the unopened package, in which the image analysis unit further acquires an optical feature amount of the jelly for swallowing by analyzing the optical image, and the quality determination unit determines the quality of the jelly for swallowing based on the first air bubble pattern and on the optical feature amount.

In addition, it is preferable that the quality determination unit detects a change in a shape of the first air bubble pattern with respect to an air bubble pattern in the jelly for swallowing in sealing the jelly for swallowing in the package, detects a change in the optical feature amount of the jelly for swallowing with respect to the optical feature amount of the jelly for swallowing in sealing the jelly for swallowing in the package, and determines the quality of the jelly for swallowing based on the change in the shape of the first air bubble pattern and on the change in the optical feature amount of the jelly for swallowing.

In addition, it is preferable that the quality determination system of a jelly for swallowing further comprises a memory in which a plurality of reference ultrasound images in which the air bubble pattern has sequentially changed in accordance with deterioration of the quality of the jelly for swallowing, and a plurality of reference optical images in which the optical feature amount of the jelly for swallowing in sealing the jelly for swallowing in the package has sequentially changed in accordance with deterioration of the quality of the jelly for swallowing are stored, in which the quality determination unit detects the change in the shape of the first air bubble pattern by comparing the ultrasound image with the plurality of reference ultrasound images stored in the memory and detects the change in the optical feature amount of the jelly for swallowing by comparing the optical image with the plurality of reference optical images stored in the memory.

In addition, it is preferable that the quality determination unit includes a first machine learning model that takes the first air bubble pattern as an input and that outputs a first estimation result obtained by estimating the quality of the jelly for swallowing, and a second machine learning model that takes the optical feature amount of the jelly for swallowing as an input and that outputs a second estimation result obtained by estimating the quality of the jelly for swallowing, and determines the quality of the jelly for swallowing by combining a first determination result obtained by determination based on the first estimation result and a second determination result obtained by determination based on the second estimation result.

In addition, it is preferable that the optical feature amount includes a color of the jelly for swallowing.

In addition, it is preferable that the optical feature amount includes a second air bubble pattern in the jelly for swallowing.

In addition, it is preferable that the quality determination unit determines the quality of the jelly for swallowing by weighting and combining a first determination result of the quality of the jelly for swallowing determined based on the first air bubble pattern and a second determination result of the quality of the jelly for swallowing determined based on the optical feature amount.

In addition, it is preferable that the quality determination unit includes a multimodal model that takes the first air bubble pattern and the optical feature amount as an input and that outputs an estimation result obtained by estimating the quality of the jelly for swallowing, and determines the quality of the jelly for swallowing based on the estimation result.

In addition, it is preferable that the quality determination system of a jelly for swallowing further comprises a residue detection unit that acquires an air bubble pattern in a residue of the jelly for swallowing by analyzing the ultrasound image generated in a state where the ultrasound probe is in contact with a pharynx part of the subject who has swallowed the jelly for swallowing, and that detects at least one of presence or absence of the residue or a region of the residue based on the air bubble pattern in the residue, in which the quality determination unit optimizes the residue detection unit based on a determination result of the quality of the jelly for swallowing.

In addition, it is preferable that the quality determination system of a jelly for swallowing further comprises an ultrasound diagnostic apparatus, and a server connected to the ultrasound diagnostic apparatus through a network, in which the ultrasound diagnostic apparatus includes the ultrasound probe and the image generation unit, and the server includes at least one of the image analysis unit, the quality determination unit, or the residue detection unit.

In addition, according to another aspect of the present invention, there is provided a quality determination method of a jelly for swallowing, the method comprising generating an ultrasound image from a reception signal obtained by transmitting and receiving an ultrasound beam in a state where an ultrasound probe is in contact with an outer surface of an unopened package in which a jelly for swallowing including air bubbles is sealed, acquiring a first air bubble pattern in the jelly for swallowing by analyzing the ultrasound image, and determining quality of the jelly for swallowing based on the first air bubble pattern.

In the present invention, it is possible to non-invasively determine the quality of the jelly for swallowing based on the first air bubble pattern in the jelly for swallowing captured in the ultrasound image. In addition, the residue detection unit optimized based on the determination result of the quality of the jelly for swallowing can examine dysphagia of the subject with high accuracy based on the air bubble pattern in the residue of the jelly for swallowing captured in the ultrasound image of the pharynx part of the subject.

DESCRIPTION OF THE PREFERRED EMBODIMENTS

Hereinafter, a quality determination system of a jelly for swallowing and a quality determination method of a jelly for swallowing according to an embodiment of the present invention will be described in detail based on preferred embodiments illustrated in the accompanying drawings.

Figure 1:
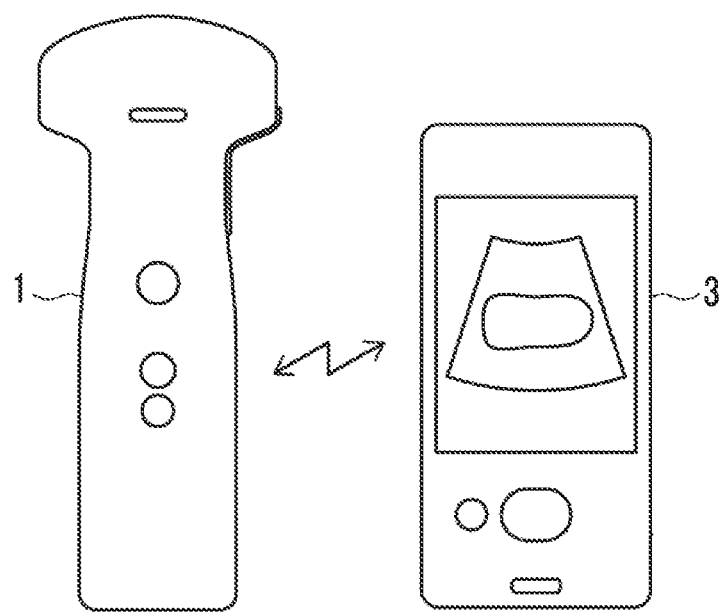
FIG. 1 is a conceptual diagram representing a configuration of an ultrasound system of a first embodiment according to the present invention.

FIG. 1 is a conceptual diagram representing a configuration of an ultrasound system of a first embodiment according to the present invention. The ultrasound system illustrated in FIG. 1 comprises an ultrasound diagnostic apparatus including an ultrasound probe 1 and an information terminal 3 of a handheld type connected to the ultrasound probe 1 in a wired or wireless manner. The ultrasound diagnostic apparatus of the present embodiment is constructed of the ultrasound probe 1, the information terminal 3 of a handheld type, and an application program for ultrasound diagnosis that operates on the information terminal 3.

Figure 2:
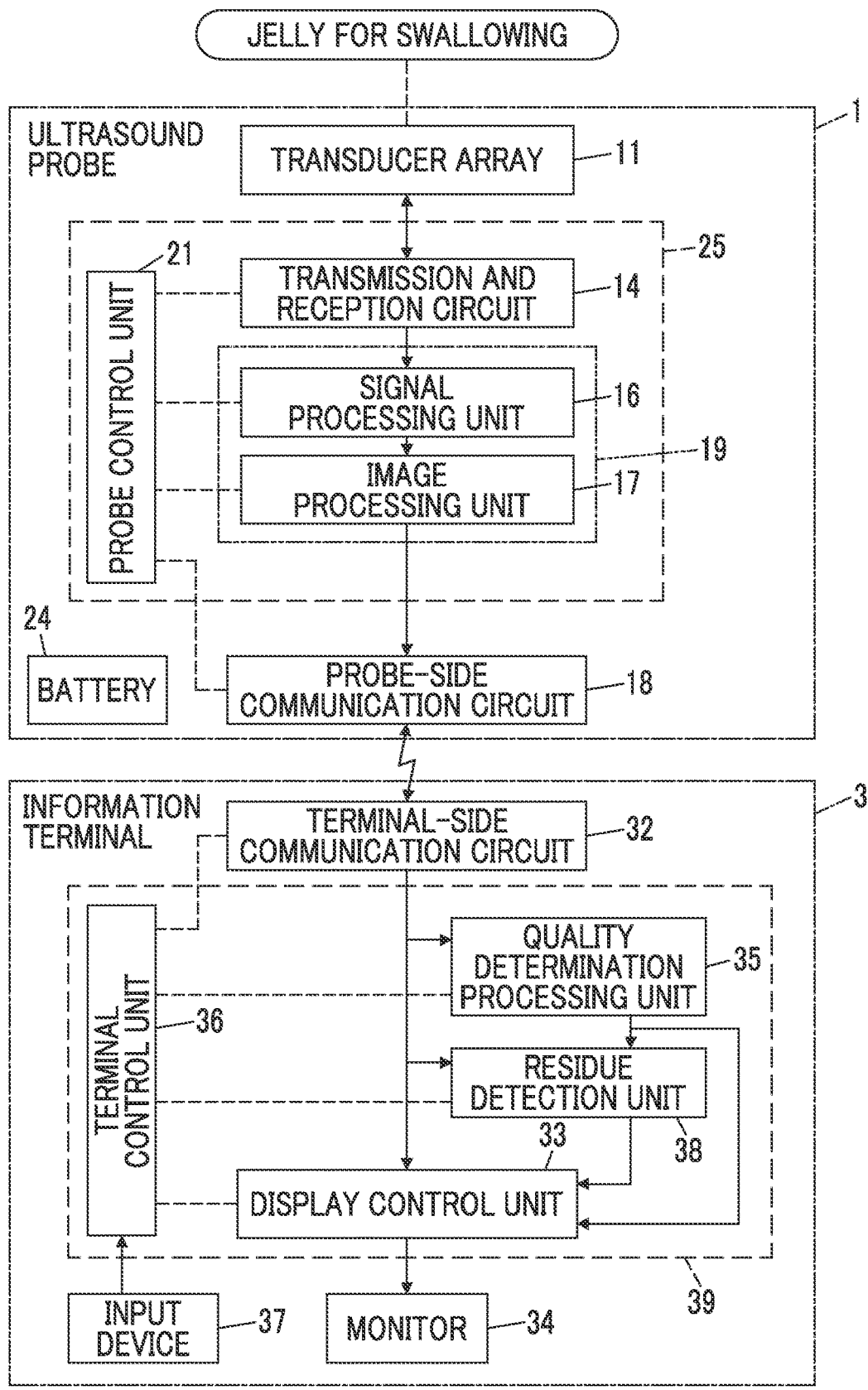
FIG. 2 is a block diagram representing a configuration of an ultrasound diagnostic apparatus of the first embodiment.

The ultrasound probe 1 captures an ultrasound image by scanning a subject with an ultrasound beam and outputs data corresponding to the ultrasound image, that is, image information data of the ultrasound image in the present embodiment. As illustrated in FIG. 2, the ultrasound probe 1 comprises a transducer array 11, a transmission and reception circuit 14, a signal processing unit 16, an image processing unit 17, a probe-side communication circuit 18, a probe control unit 21, and a battery 24.

The transmission and reception circuit 14 is bidirectionally connected to the transducer array 11. The signal processing unit 16, the image processing unit 17, and the probe-side communication circuit 18 are sequentially connected in series to the transmission and reception circuit 14. The signal processing unit 16 and the image processing unit 17 constitute an image information data generation unit 19. The probe control unit 21 is connected to the transmission and reception circuit 14, the signal processing unit 16, the image processing unit 17, and the probe-side communication circuit 18. In addition, the ultrasound probe 1 incorporates the battery 24.

The transmission and reception circuit 14, the image information data generation unit 19 (the signal processing unit 16 and the image processing unit 17), and the probe control unit 21 constitute a probe-side processor 25.

The transducer array 11 includes a plurality of ultrasound oscillators that are one-dimensionally or two-dimensionally arranged. Each of the oscillators transmits an ultrasound wave in accordance with a drive signal supplied from the transmission and reception circuit 14 and outputs an analog reception signal by receiving a reflected wave from the subject.

Each oscillator is configured by forming an electrode at both ends of a piezoelectric body consisting of, for example, a piezoelectric ceramic represented by lead zirconate titanate (PZT), a polymer piezoelectric element represented by polyvinylidene difluoride (PVDF), and a piezoelectric single crystal represented by lead magnesium niobate-lead titanate (PMN-PT).

Figure 3:
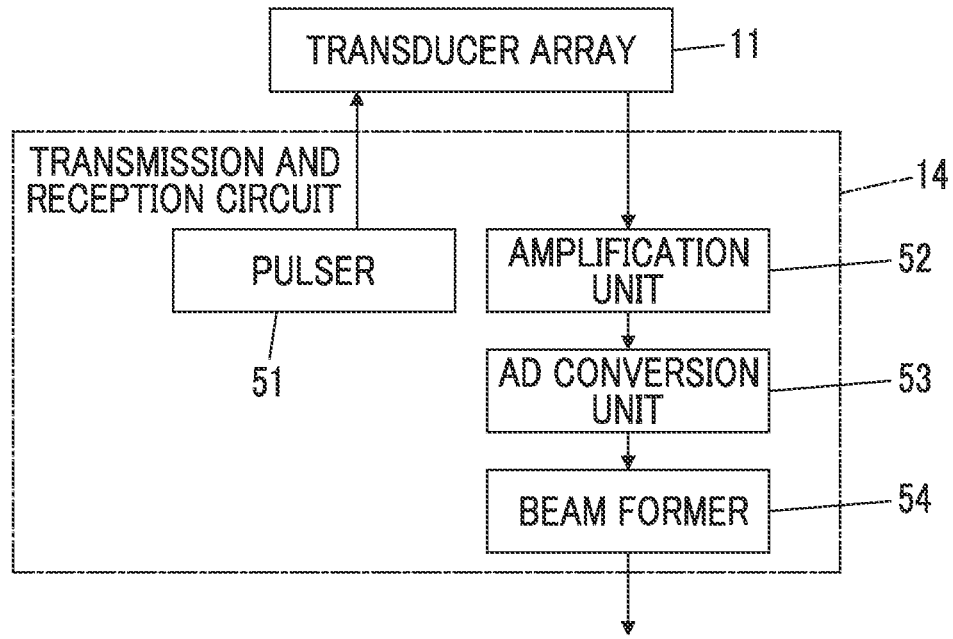
FIG. 3 is a block diagram representing a configuration of a transmission and reception circuit of the first embodiment.

The transmission and reception circuit 14, under control of the probe control unit 21, transmits an ultrasound wave from the transducer array 11 and performs reception focus processing on a reception signal output from the transducer array 11 that has received an ultrasound echo, thereby generating a sound ray signal. As illustrated in FIG. 3, the transmission and reception circuit 14 includes a pulser 51 connected to the transducer array 11, and an amplification unit 52, an analog digital (AD) conversion unit 53, and a beam former 54 that are sequentially connected in series from the transducer array 11.

The pulser 51 includes, for example, a plurality of pulse generators and supplies each drive signal to the plurality of oscillators by adjusting a delay amount of each drive signal based on a transmission delay pattern selected by the probe control unit 21 so that the ultrasound waves transmitted from the plurality of oscillators of the transducer array 11 form an ultrasound beam. In a case where a voltage having a pulse shape or a continuous wave shape is applied to the electrodes of the oscillators of the transducer array 11, the piezoelectric body expands and contracts to generate an ultrasound wave having a pulse shape or a continuous wave shape from each oscillator, and an ultrasound beam is formed from a combined wave of the ultrasound waves.

The transmitted ultrasound beam is reflected by, for example, a target such as a part of the subject and propagates toward the transducer array 11 of the ultrasound probe 1. By receiving the ultrasound echo propagating toward the transducer array 11, each oscillator constituting the transducer array 11 expands and contracts to generate the reception signal that is an electric signal, and outputs the reception signal to the amplification unit 52.

The amplification unit 52 amplifies the signal input from each oscillator constituting the transducer array 11 and transmits the amplified signal to the AD conversion unit 53. The AD conversion unit 53 converts the signal transmitted from the amplification unit 52 into digital reception data and outputs the reception data to the beam former 54.

The beam former 54 performs so-called reception focus processing by applying a delay to each reception data received from the AD conversion unit 53 and by adding each reception data in accordance with a sound speed or with a distribution of the sound speed set based on a reception delay pattern selected by the probe control unit 21. Through the reception focus processing, the sound ray signal in which each reception data converted by the AD conversion unit 53 is phased and added, and in which a focus of the ultrasound echo is narrowed is generated.

The image information data generation unit 19 generates the image information data based on the sound ray signal generated by the transmission and reception circuit 14. As described above, the image information data generation unit 19 includes the signal processing unit 16 and the image processing unit 17.

The signal processing unit 16, under control of the probe control unit 21, generates image signal data before capturing as the ultrasound image based on the sound ray signal generated by the transmission and reception circuit 14. More specifically, the signal processing unit 16 generates a signal representing tomographic image information related to tissues in the subject as the image signal data before capturing by performing signal processing, for example, correction of attenuation by a propagation distance in accordance with depths of positions at which the ultrasound waves are reflected, and then, by performing envelope detection processing with respect to the sound ray signal generated by the beam former 54 of the transmission and reception circuit 14.

The image processing unit 17, under control of the probe control unit 21, generates the ultrasound image as the image information data generated by the image information data generation unit 19 based on the image signal data generated by the signal processing unit 16. More specifically, the image processing unit 17 generates the ultrasound image (ultrasound image signal) by performing raster conversion of the image signal data before capturing generated by the signal processing unit 16 into an image signal complying with a scanning method of a typical television signal and by performing, on the converted image signal, various types of image processing such as brightness correction, gradation correction, sharpness correction, image size correction, refresh rate correction scanning frequency correction, and color correction complying with a display format of a monitor 34 and then, outputs the ultrasound image generated by the image information data generation unit 19 to the probe-side communication circuit 18 as the image information data.

The transmission and reception circuit 14, the signal processing unit 16, and the image processing unit 17 constitute an image generation unit according to the embodiment of the present invention.

The image generation unit generates the ultrasound image, that is, the ultrasound image as the image information data in the present embodiment, from the reception signal obtained by transmitting and receiving the ultrasound beam to and from the subject using the ultrasound probe 1 (more precisely, the transducer array 11).

The probe-side communication circuit 18, under control of the probe control unit 21, transmits the image information data generated by the image processing unit 17 in a wired or wireless manner. In the present embodiment, the probe-side communication circuit 18 includes an antenna for transmission and reception of radio waves and wirelessly transmits the ultrasound image by modulating a carrier based on the ultrasound image generated by the image processing unit 17 to generate a transmission signal and by supplying the transmission signal to the antenna to transmit radio waves from the antenna.

Amplitude shift keying (ASK), phase shift keying (PSK), quadrature phase shift keying (QPSK), 16 quadrature amplitude modulation (16QAM), or the like is used as a method of modulating the carrier.

In addition, the probe-side communication circuit 18 can also connect the ultrasound probe 1 to the information terminal 3 in a wired manner using a cable such as a universal serial bus (USB) cable.

The probe control unit 21 controls each part of the ultrasound probe 1 based on a program and the like stored in advance. More specifically, the probe control unit 21 controls the transmission and reception circuit 14 to transmit the ultrasound beam and receive the ultrasound echo based on an examination mode and a scanning method set in advance. In addition, the probe control unit 21 controls the signal processing unit 16 and the image processing unit 17 of the image information data generation unit 19 to perform signal processing set in advance on the sound ray signal and to perform image processing set in advance on the image signal data. Furthermore, the probe control unit 21 controls the probe-side communication circuit 18 to transmit the image signal data with radio wave transmission strength set in advance.

Here, it is assumed that the examination mode indicates any of examination modes usable in the ultrasound diagnostic apparatus, such as a brightness (B) mode, a color doppler (CF) mode, a power doppler (PD) mode, a motion (M) mode, a pulse doppler (PW) mode, and a continuous wave doppler (CW) mode, and that the scanning method indicates any of scanning methods such as an electronic sector scanning method, an electronic linear scanning method, and an electronic convex scanning method.

The battery 24 is incorporated in the ultrasound probe 1 and supplies power to each circuit of the ultrasound probe 1.

Next, the information terminal 3 is a terminal apparatus of a handheld type such as a smartphone and a tablet personal computer (PC) and displays the ultrasound image based on data corresponding to the ultrasound image captured by the ultrasound probe 1. As illustrated in FIG. 2, the information terminal 3 comprises a terminal-side communication circuit 32, a display control unit 33, a quality determination processing unit 35, a residue detection unit 38, a terminal control unit 36, the monitor 34, and an input device 37.

The display control unit 33 and the monitor 34 are sequentially connected in series to the terminal-side communication circuit 32. In addition, the quality determination processing unit 35 and the residue detection unit 38 are connected to the terminal-side communication circuit 32, and the residue detection unit 38 is connected to the quality determination processing unit 35. Furthermore, the display control unit 33 is connected to the quality determination processing unit 35 and to the residue detection unit 38. The terminal control unit 36 is connected to the terminal-side communication circuit 32, the display control unit 33, the quality determination processing unit 35, and the residue detection unit 38, and the input device 37 is connected to the terminal control unit 36.

In the present embodiment, the probe-side communication circuit 18 of the ultrasound probe 1 is wirelessly connected to the terminal-side communication circuit 32 of the information terminal 3 by wireless communication. Accordingly, the ultrasound probe 1 and the information terminal 3 are connected to be capable of bidirectionally exchanging information.

The terminal-side communication circuit 32, under control of the terminal control unit 36, receives the image information data transmitted from the probe-side communication circuit 18 of the ultrasound probe 1 in a wired or wireless manner. In the present embodiment, the terminal-side communication circuit 32 includes an antenna for transmission and reception of radio waves and outputs the ultrasound image (ultrasound image signal) that is the image information data by receiving the transmission signal wirelessly transmitted from the probe-side communication circuit 18 through the antenna and by demodulating the received transmission signal.

The display control unit 33 displays various types of information on the monitor 34 under control of the terminal control unit 36. For example, the display control unit 33 performs predetermined processing on the ultrasound image, which is the image information data received by the terminal-side communication circuit 32, and displays the ultrasound image on the monitor 34. In addition, the display control unit 33 displays various messages, various operation screens, and the like on the monitor 34.

The monitor 34 displays various types of information. As described above, the monitor 34 displays not only the ultrasound image but also various messages, various operation screens, and the like under control of the display control unit 33. Examples of the monitor 34 include a liquid crystal display (LCD) and an organic electro-luminescence (EL) display.

The input device 37 is used for a user to input various instructions by performing an input operation and, in the present embodiment, includes a touch panel or the like with which the user can input various instructions by performing a touch operation.

Figure 4:
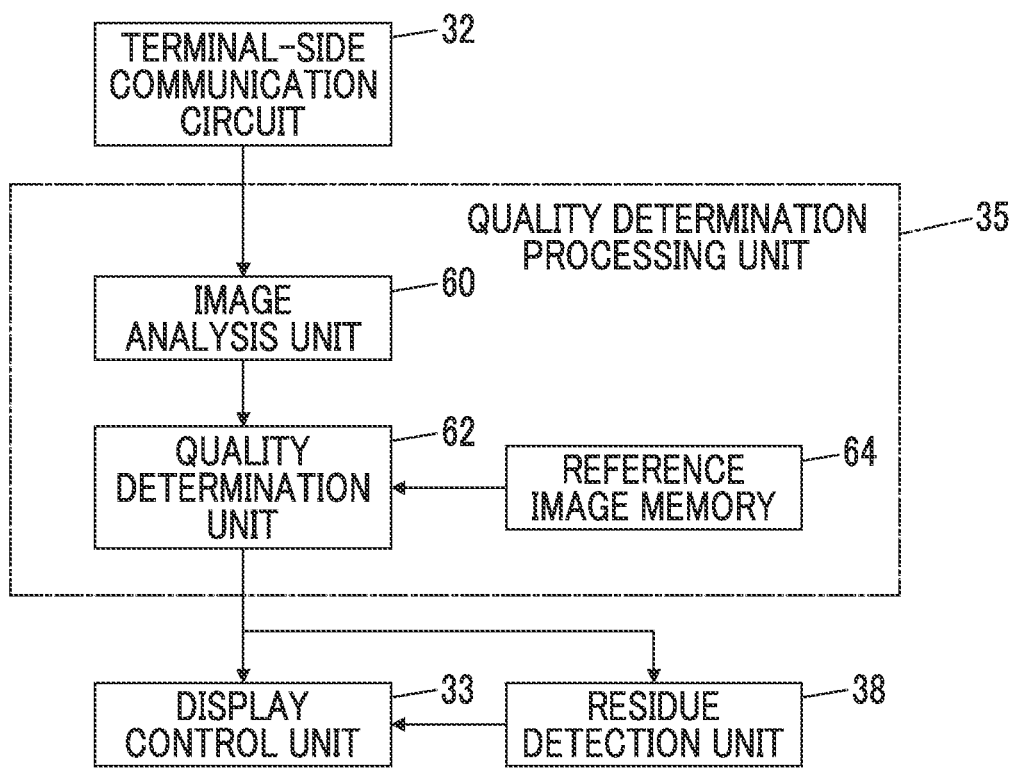
FIG. 4 is a block diagram representing a configuration of a quality determination processing unit of the first embodiment.

The quality determination processing unit 35 performs various types of processing related to determination of quality of the jelly for swallowing under control of the terminal control unit 36. As illustrated in FIG. 4, the quality determination processing unit 35 includes an image analysis unit 60, a quality determination unit 62, and a reference image memory 64. The image analysis unit 60 is connected to the terminal-side communication circuit 32. The quality determination unit 62 is connected to the image analysis unit 60 and to the reference image memory 64, and the display control unit 33 and the residue detection unit 38 are connected to the quality determination unit 62.

The image analysis unit 60 acquires a first air bubble pattern in the jelly for swallowing captured in the ultrasound image by analyzing the ultrasound image generated in a state where the ultrasound probe 1 is in contact with an outer surface of an unopened package in which the jelly for swallowing including air bubbles is sealed.

For example, the jelly for swallowing is a general edible jelly of which a best before period is set to six months, and is stored in a cool dark place, a refrigerator of 10° C. or lower, or the like. The air bubbles included in the jelly for swallowing are not particularly limited and are granular air bubbles such as carbonic acid gas having a size in diameter of approximately 1 to 2 mm. In addition, in the jelly for swallowing, a predetermined number of air bubbles are sealed in a predetermined region-of-interest with predetermined density and predetermined uniformity. The number of air bubbles, the sizes of the air bubbles, the density of the air bubbles, the uniformity of the air bubbles, and the like are not particularly limited.

Figure 10:
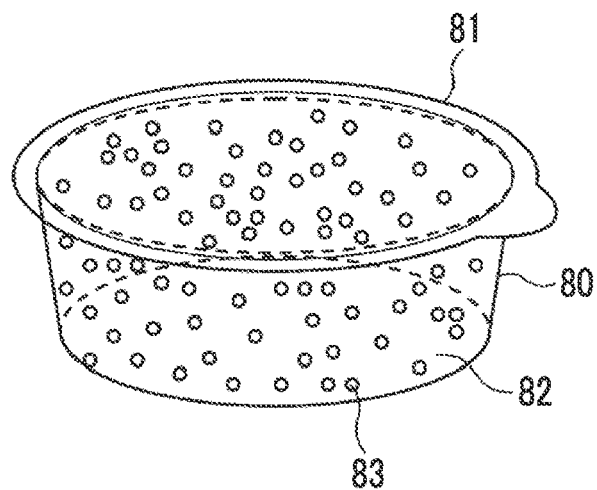
FIG. 10 is a conceptual diagram representing a package in which a jelly for swallowing is sealed.

For example, as illustrated in FIG. 10, the package of the jelly for swallowing includes a cup 80 and an upper lid 81. A jelly for swallowing 82 is accommodated in the cup 80 having an upper opening portion and is sealed in the package by sealing the upper opening portion of the cup 80 with the upper lid 81.

The user can capture an ultrasound image of the jelly for swallowing 82 sealed in the package in a state where the ultrasound probe 1 is in contact with an outer surface of the cup 80 or in a state where the ultrasound probe 1 is in contact with an outer surface of the upper lid 81 in a case where the jelly for swallowing 82 is in contact with the upper lid 81 with no air layer therebetween. In imaging, for example, an ultrasound wave of approximately 5 MHz to 10 MHz is transmitted in order to individually image air bubbles 83 in the jelly for swallowing 82.

The image analysis unit 60 acquires, as the first air bubble pattern, a feature amount of the air bubbles of at least one of the number of air bubbles, the sizes of the air bubbles, the density of the air bubbles, or the uniformity of the air bubbles. The image analysis unit 60 may acquire other feature amounts of the air bubbles.

The image analysis unit 60 is not particularly limited and can acquire the first air bubble pattern by analyzing the ultrasound image using a machine learning model that is trained using deep learning or the like, or well-known various image analysis technologies or the like.

For example, the machine learning model of the image analysis unit 60 is a trained model that uses an ultrasound image for learning obtained by imaging the unopened package in which the jelly for swallowing including the air bubbles is sealed, and an air bubble pattern of the jelly for swallowing captured in the ultrasound image for learning as training data, and that has learned about a relationship between the ultrasound image for learning and the air bubble pattern of the jelly for swallowing captured in the ultrasound image for learning for a plurality of pieces of the training data.

The machine learning model takes the ultrasound image obtained by imaging the unopened package in which the jelly for swallowing including the air bubbles is sealed, as an input and outputs an estimation result obtained by estimating the first air bubble pattern of the jelly for swallowing captured in the ultrasound image.

The image analysis unit 60 acquires the first air bubble pattern in the jelly for swallowing based on the estimation result obtained by estimation by the machine learning model.

The reference image memory 64 is a memory that stores a plurality of reference ultrasound images in which the air bubble pattern in the jelly for swallowing in sealing the jelly for swallowing in the package has sequentially changed in accordance with deterioration of the quality of the jelly for swallowing.

Here, for example, deterioration of the quality of the jelly for swallowing includes not only deterioration of the quality over time but also deterioration of the quality in accordance with a change in temperature and deterioration of the quality in accordance with irradiation with ultraviolet rays or with direct sunlight. In addition, other causes of deterioration of the quality may be included. The reference image memory 64 can store the plurality of reference ultrasound images that have sequentially changed in accordance with one or a combination of two or more causes of deterioration of the quality, by combining one or two or more causes of deterioration of the quality.

For example, the air bubble pattern in the jelly for swallowing deteriorates over time and changes in shape. For example, air bubbles are integrated by coming into contact with each other. Accordingly, gradually, air bubbles are increased in size, the number of air bubbles is decreased, the density of the air bubbles is decreased, and the uniformity of the air bubbles deteriorates. The same applies to other causes of deterioration. Deterioration of the air bubble pattern is accelerated in accordance with a change in temperature or with an increase in an irradiation time with ultraviolet rays or with direct sunlight, and the air bubble pattern may not be usable in a case of examining dysphagia even in the best before period.

The quality determination unit 62 determines the quality of the jelly for swallowing based on the first air bubble pattern acquired by the image analysis unit 60. In addition, the quality determination unit 62 optimizes the residue detection unit 38 based on a determination result of the quality of the jelly for swallowing.

The quality determination unit 62 can also determine the quality of the jelly for swallowing using a machine learning model or well-known various image analysis technologies or the like.

For example, the machine learning model of the quality determination unit 62 is a trained model that uses the air bubble pattern in the jelly for swallowing captured in the ultrasound image for learning and the quality of the jelly for swallowing as training data, and that has learned about a relationship between the air bubble pattern in the jelly for swallowing captured in the ultrasound image for learning and the quality of the jelly for swallowing for a plurality of pieces of the training data.

The machine learning model takes the first air bubble pattern in the jelly for swallowing captured in the ultrasound image as an input and outputs an estimation result obtained by estimating the quality of the jelly for swallowing.

The quality determination unit 62 determines the quality of the jelly for swallowing based on the estimation result obtained by estimation by the machine learning model.

The residue detection unit 38, under control of the terminal control unit 36, acquires an air bubble pattern in a residue of the jelly for swallowing remaining in a pharynx part, for example, a pyriform sinus, of the subject in swallowing by analyzing the ultrasound image generated in a state where the ultrasound probe 1 is in contact with the pharynx part of the subject who has swallowed the jelly for swallowing, and detects presence or absence of the residue or the like based on the air bubble pattern in the residue of the jelly for swallowing. Furthermore, the residue detection unit 38 can detect a region of the residue by semantic segmentation, detection based on a bounding box, and the like.

The residue detection unit 38 can also detect the presence or absence of the residue of swallowing, the region of the residue, and the like using a machine learning model or well-known various image analysis technologies or the like.

For example, the machine learning model of the residue detection unit 38 is a trained model that uses an ultrasound image for learning of the pharynx part of the subject and at least one of the presence or absence of the residue of swallowing or the region in the ultrasound image for learning as training data, and that has learned about a relationship between the ultrasound image for learning and at least one of the presence or absence of the residue of swallowing or the region in the ultrasound image for learning for a plurality of pieces of the training data.

The machine learning model takes the ultrasound image of the pharynx part of the subject as an input and outputs an estimation result obtained by estimating at least one of the presence or absence of the residue of swallowing or the region in the ultrasound image.

The residue detection unit 38 detects at least one of the presence or absence of the residue of swallowing or the region based on the estimation result obtained by estimation by the machine learning model.

The display control unit 33, the quality determination processing unit 35, the residue detection unit 38, and the terminal control unit 36 constitute a terminal-side processor 39.

In addition, in the ultrasound system of the first embodiment, at least the ultrasound probe 1 (transducer array 11), the image generation unit, and the quality determination processing unit 35 including the image analysis unit 60, the quality determination unit 62, and the reference image memory 64 constitute the quality determination system of a jelly for swallowing according to the embodiment of the present invention.

Figure 5:
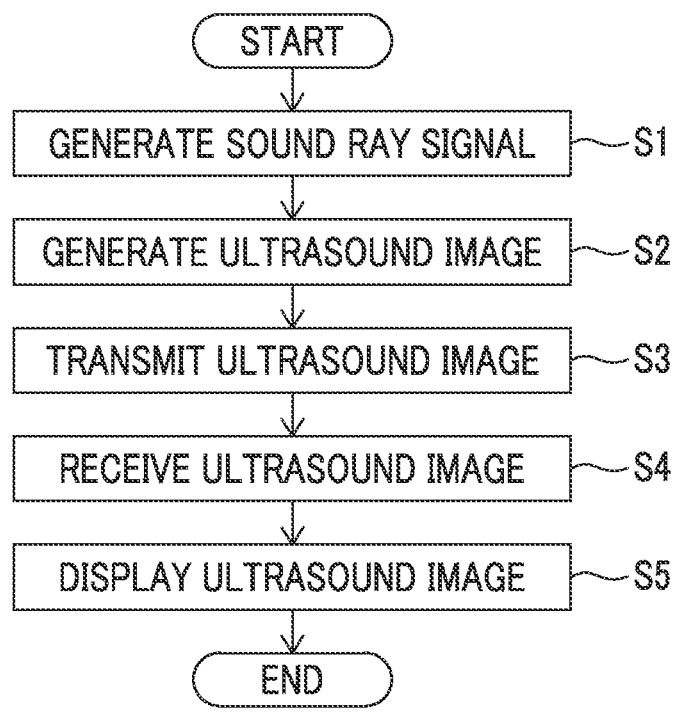
FIG. 5 is a flowchart of one embodiment representing operation of the ultrasound system of the first embodiment in a case of capturing an ultrasound image.

Next, operation of the ultrasound system of the first embodiment in capturing the ultrasound image will be described with reference to the flowchart in FIG. 5.

The transmission and reception circuit 14 starts transmitting the ultrasound wave based on an instruction of the user input from the input device 37 in a state where the ultrasound probe 1 is in contact with a body surface of the subject, and the sound ray signal is generated (step S1).

That is, the ultrasound beam is transmitted into the subject from the plurality of oscillators of the transducer array 11 in accordance with the drive signals from the pulser 51 of the transmission and reception circuit 14 under control of the probe control unit 21.

The ultrasound echo from the subject based on the ultrasound beam transmitted from the pulser 51 is received by each oscillator of the transducer array 11, and the reception signal that is an analog signal is output from each oscillator of the transducer array 11 that has received the ultrasound echo.

The reception signal that is an analog signal output from each oscillator of the transducer array 11 is amplified by the amplification unit 52 of the transmission and reception circuit 14 and is subjected to AD conversion by the AD conversion unit 53 to be acquired as the reception data.

The sound ray signal is generated by performing the reception focus processing on the reception data via the beam former 54.

Next, the image information data generation unit 19 generates the ultrasound image as the image information data based on the sound ray signal generated by the beam former 54 of the transmission and reception circuit 14 (step S2).

That is, the signal processing unit 16 of the image information data generation unit 19 performs various types of signal processing on the sound ray signal generated by the beam former 54 to generate the signal representing the tomographic image information related to tissues in the subject as the image signal data before capturing.

The image processing unit 17 performs the raster conversion and further performs various types of image processing on the image signal data generated by the signal processing unit 16 to generate the ultrasound image as the image information data.

The ultrasound image generated by the image processing unit 17 is wirelessly transmitted toward the information terminal 3 from the probe-side communication circuit 18 (step S3).

Next, the terminal-side communication circuit 32 receives the ultrasound image wirelessly transmitted from the probe-side communication circuit 18 of the ultrasound probe 1 under control of the terminal control unit 36 of the information terminal 3 (step S4).

Next, the display control unit 33 performs the predetermined processing on the ultrasound image received by the terminal-side communication circuit 32 and displays the ultrasound image on the monitor 34 (step S5).

Figure 6:
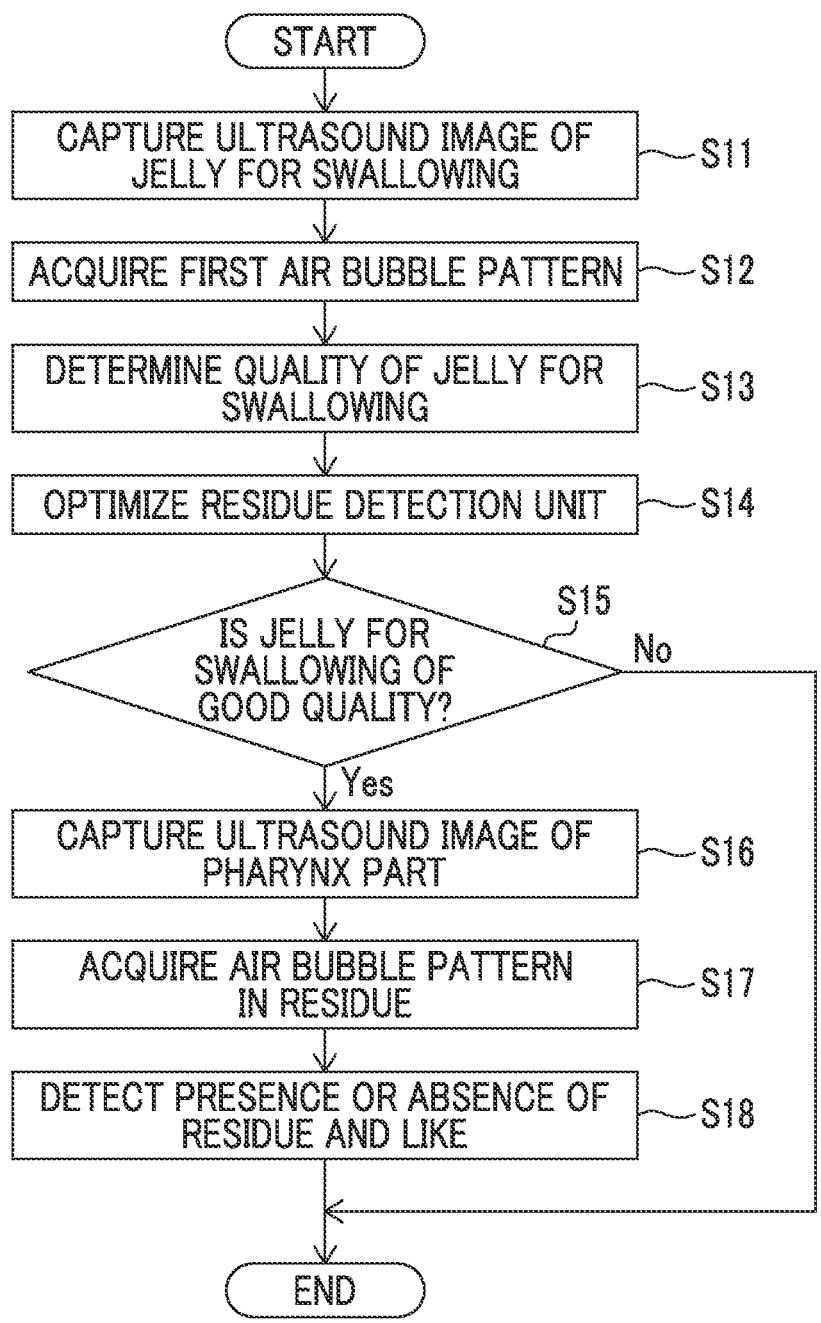
FIG. 6 is a flowchart of one embodiment representing operation of the ultrasound system of the first embodiment in a case of examining dysphagia.

Next, operation of the ultrasound system of the first embodiment in a case of examining dysphagia will be described with reference to the flowchart in FIG. 6.

First, the user images a package of the jelly for swallowing of which the quality is to be determined, that is, the unopened package in which the jelly for swallowing including the air bubbles is sealed (step S11).

In this case, the transmission and reception circuit 14 starts transmitting the ultrasound wave in a state where the ultrasound probe 1 is in contact with the outer surface of the package of the jelly for swallowing, and the sound ray signal is generated.

Next, the image information data generation unit 19 generates the ultrasound image obtained by imaging the package of the jelly for swallowing based on the sound ray signal generated by the transmission and reception circuit 14.

The ultrasound image of the jelly for swallowing is transmitted to the information terminal 3 from the ultrasound probe 1 and is received by the terminal-side communication circuit 32 of the information terminal 3.

Next, the display control unit 33 performs the predetermined processing on the ultrasound image of the jelly for swallowing received by the terminal-side communication circuit 32 and displays the ultrasound image on the monitor 34.

While any of a linear type, a sector type, or a convex type of the ultrasound probe 1 can be used, it is preferable that the ultrasound probe 1 of a linear type or of a sector type having a relatively small contact surface is used because a size of the package of the jelly for swallowing is relatively small.

Figure 11:
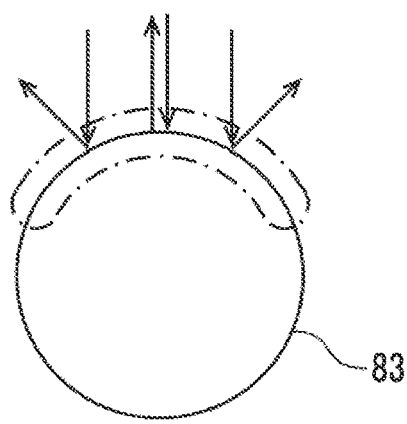
FIG. 11 is a conceptual diagram representing a state where an ultrasound wave is reflected on a surface of an air bubble.
Figure 12:
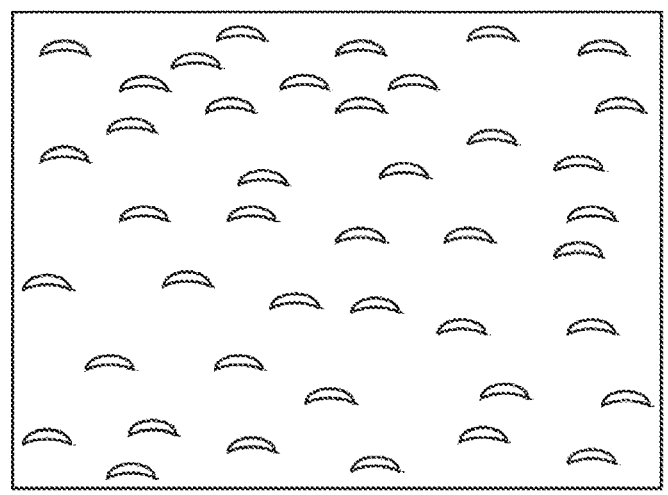
FIG. 12 is a conceptual diagram representing an air bubble pattern captured in the ultrasound image.

Here, in a case of capturing the ultrasound image of the jelly for swallowing, there is a large difference in impedance between the carbonic acid gas or the like of the air bubbles 83 and the jelly for swallowing. Thus, as illustrated in FIG. 11, the ultrasound wave is subjected to total reflection on surfaces of the air bubbles 83, and a crescent-shaped part surrounded by a dot-dashed line is depicted as an ultrasound tomographic image of high brightness. Consequently, as illustrated in FIG. 12, a plurality of crescent-shaped ultrasound tomographic images of high brightness corresponding to the plurality of air bubbles 83 are included in the ultrasound image of the jelly for swallowing.

Next, the image analysis unit 60 analyzes the ultrasound image of the jelly for swallowing received by the terminal-side communication circuit 32 and acquires the first air bubble pattern in the jelly for swallowing captured in the ultrasound image of the jelly for swallowing (step S12).

Next, the quality determination unit 62 determines the quality of the jelly for swallowing based on the first air bubble pattern acquired by the image analysis unit 60 (step S13).

For example, the quality determination unit 62 detects a change in a shape of the first air bubble pattern with respect to the air bubble pattern in the jelly for swallowing in sealing the jelly for swallowing in the package and determines the quality of the jelly for swallowing based on the change in the shape of the first air bubble pattern. In other words, the quality determination unit 62 detects similarity between the shape of the air bubble pattern in the jelly for swallowing in sealing the jelly for swallowing in the package and the shape of the first air bubble pattern, and determines the quality of the jelly for swallowing based on the similarity.

For example, the quality determination unit 62 determines that the quality of the jelly for swallowing deteriorates more as the air bubbles are increased in size. In addition, the quality determination unit 62 determines that the quality of the jelly for swallowing more deteriorates as the number of air bubbles is decreased, determines that the quality of the jelly for swallowing more deteriorates as the density of the air bubbles is decreased, and determines that the quality of the jelly for swallowing more deteriorates as the uniformity of the air bubbles deteriorates.

A method of detecting the change in the shape of the first air bubble pattern is not particularly limited. For example, a plurality of reference ultrasound images in which the air bubble pattern has sequentially changed in accordance with deterioration of the quality of the jelly for swallowing can be stored in the reference image memory 64, and the change in the shape of the first air bubble pattern can be detected by comparing the ultrasound image of the jelly for swallowing with the plurality of reference ultrasound images stored in the reference image memory 64. Accordingly, it is possible to determine the quality of the jelly for swallowing in a plurality of levels based on the change in the shape of the first air bubble pattern.

In a case where the determination of the quality of the jelly for swallowing ends, the quality determination unit 62 optimizes the residue detection unit 38 based on the determination result of the quality of the jelly for swallowing (step S14).

For example, the residue detection unit 38 includes a plurality of machine learning models corresponding to a plurality of air bubble patterns in which the number of air bubbles, the sizes of the air bubbles, the density of the air bubbles, and the uniformity of the air bubbles are different. The quality determination unit 62 optimizes the residue detection unit 38 by switching the plurality of machine learning models of the residue detection unit 38 based on the determination result of the jelly for swallowing. For example, in a case where it is determined that the number of air bubbles is small as a result of the determination of the jelly for swallowing, the quality determination unit 62 optimizes the residue detection unit 38 by switching to a machine learning model corresponding to an air bubble pattern in which the number of air bubbles is small. Accordingly, the residue detection unit 38 can detect the presence or absence of the residue of the jelly for swallowing, the region of the residue, and the like using the optimal machine learning model corresponding to the quality of the jelly for swallowing.

A method for optimizing the residue detection unit 38 is not particularly limited. For example, a parameter of the machine learning model may be changed, the number of layers of the machine learning model may be changed, or a module of each layer may be changed. Other optimization methods may also be used.

Next, the display control unit 33 displays the determination result of the quality of the jelly for swallowing and information related to the optimization of the residue detection unit 38 on the monitor 34. For example, a message such as "Change in number of air bubbles is detected, and machine learning model is optimized" is displayed. Accordingly, the user can check the quality of the jelly for swallowing and determine whether or not the jelly for swallowing can be used in a case of examining dysphagia. In addition, the user can check that the residue detection unit 38 is optimized.

What is to be displayed as the determination result is not particularly limited. For example, which level the quality of the jelly for swallowing is in among the plurality of levels, or a message related to a change in the number of air bubbles, a change in the sizes of the air bubbles, a change in the density of the air bubbles, a change in the uniformity of the air bubbles, and the like can be displayed.

What is to be displayed as the information related to the optimization is also not particularly limited. Various types of information related to the optimization of the residue detection unit 38 can be displayed. The information related to the optimization may be displayed or may not be displayed.

Here, in a case where the user determines that the jelly for swallowing is not of good quality by referring to the determination result of the quality of the jelly for swallowing (No in step S15), subsequent processing ends. In this case, the user can repeat processing from the beginning by selecting the jelly for swallowing of which the quality is to be determined again.

On the other hand, in a case where the user determines that the jelly for swallowing is of good quality (Yes in step S15), the ultrasound image of the pharynx part of the subject is captured (step S16).

In this case, the transmission and reception circuit 14 starts transmitting the ultrasound wave in a state where the ultrasound probe 1 is in contact with the pharynx part, for example, one pharynx part of left and right pharynx parts, of the subject who has swallowed the jelly for swallowing determined as being of good quality. The ultrasound image of the pharynx part of the subject is captured. Subsequent operation is the same as in a case where the package of the jelly for swallowing is imaged. The ultrasound image obtained by imaging the pharynx part of the subject is displayed on the monitor 34.

Next, the residue detection unit 38 analyzes the ultrasound image of the pharynx part of the subject and acquires the air bubble pattern in the residue of the jelly for swallowing (step S17), and detects the presence or absence of the residue, the region of the residue, and the like based on the air bubble pattern in the residue of the jelly for swallowing (step S18).

In the ultrasound system of the first embodiment, it is possible to non-invasively determine the quality of the jelly for swallowing based on the first air bubble pattern in the jelly for swallowing captured in the ultrasound image. In addition, the residue detection unit 38 optimized based on the determination result of the quality of the jelly for swallowing can examine dysphagia of the subject with high accuracy based on the air bubble pattern in the residue of the jelly for swallowing captured in the ultrasound image of the pharynx part of the subject.

Figure 7:
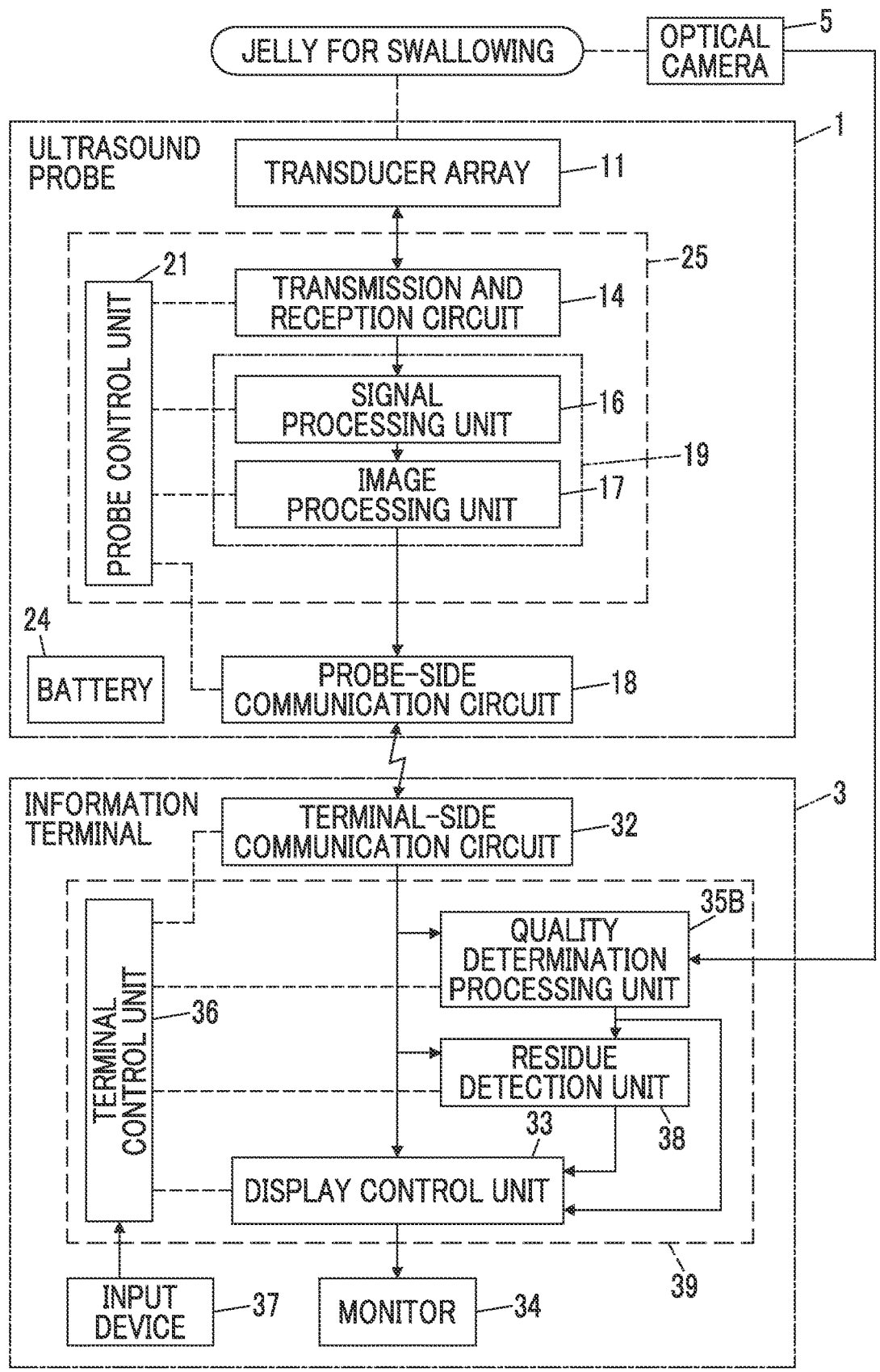
FIG. 7 is a conceptual diagram representing a configuration of an ultrasound system of a second embodiment according to the present invention.

Next, FIG. 7 is a conceptual diagram representing a configuration of an ultrasound system of a second embodiment according to the present invention. The ultrasound system of the second embodiment illustrated in FIG. 7 comprises a quality determination processing unit 35B instead of the quality determination processing unit 35 of the ultrasound system of the first embodiment illustrated in FIG. 1, and further comprises an optical camera 5. The quality determination processing unit 35B is connected to the optical camera 5. Hereinafter, the optical camera 5 and the quality determination processing unit 35B will be mainly described.

The optical camera 5 is an example of an optical image acquisition unit according to the embodiment of the present invention and captures various optical images. For example, the optical camera 5 acquires an optical image of the unopened package in which the jelly for swallowing including the air bubbles is sealed. The optical camera 5 is not particularly limited and may be various digital cameras, for example, a digital single lens reflex camera or a digital camera comprised in a smartphone or the like which is the information terminal 3. In addition, the optical image may be a still image or a video image.

In the ultrasound system of the second embodiment, the cup 80 and the upper lid 81 of the package of the jelly for swallowing illustrated in FIG. 10 are formed of a substantially transparent material. At least a part of the cup 80 or the upper lid 81 may be formed of a substantially transparent material.

The user can capture an optical image of the jelly for swallowing 82 sealed in the package in a state where the ultrasound probe 1 is in contact with a substantially transparent part of the outer surface of the package.

Figure 8:
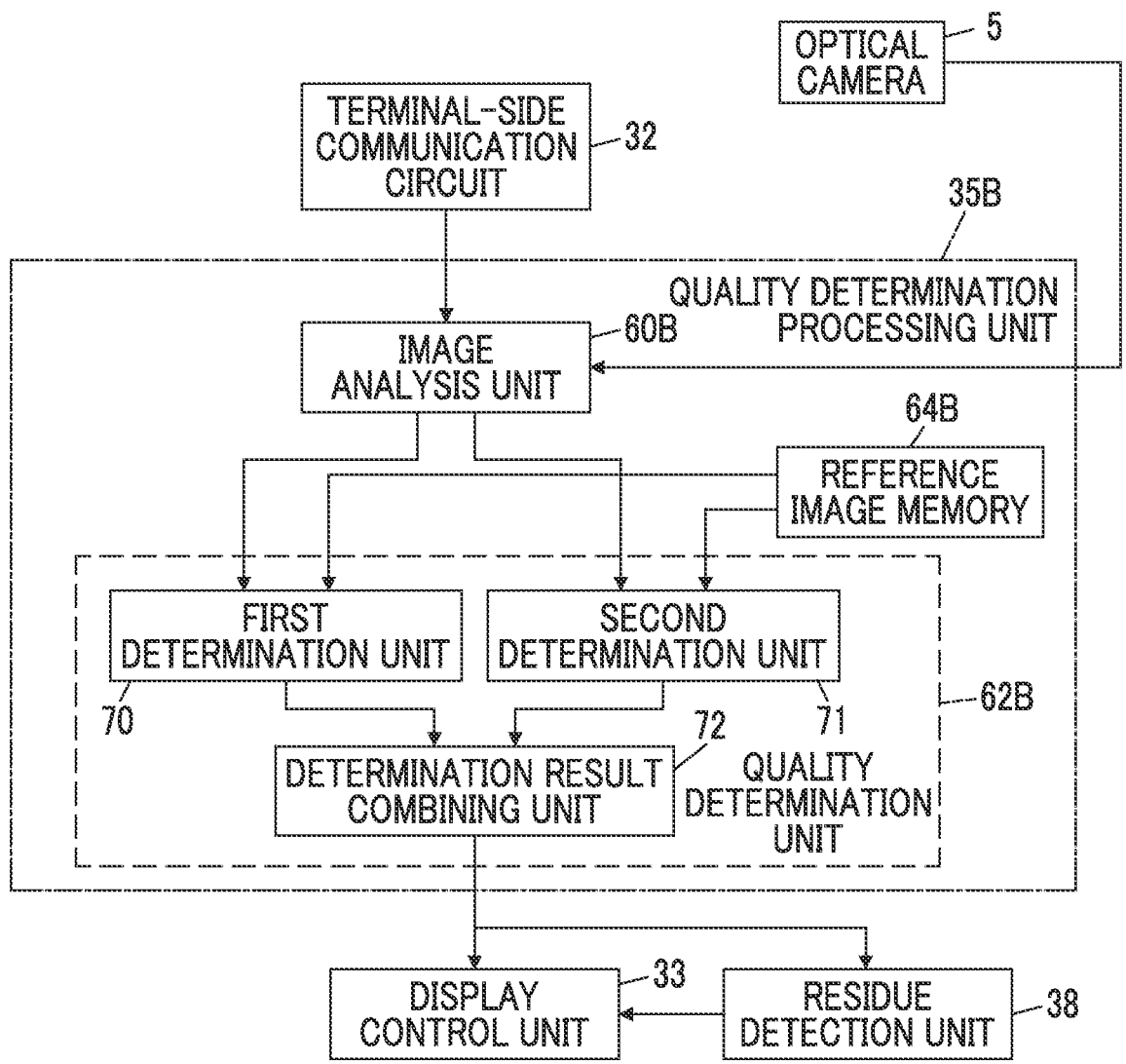
FIG. 8 is a block diagram representing a configuration of a quality determination processing unit of the second embodiment.

The quality determination processing unit 35B, in the same manner as the quality determination processing unit 35 of the first embodiment, performs various types of processing related to the determination of the quality of the jelly for swallowing under control of the terminal control unit 36. As illustrated in FIG. 8, the quality determination processing unit 35B includes an image analysis unit 60B, a reference image memory 64B, and a quality determination unit 62B. The image analysis unit 60B is connected to the terminal-side communication circuit 32. The quality determination unit 62B is connected to the image analysis unit 60B and to the reference image memory 64B, and the display control unit 33 and the residue detection unit 38 are connected to the quality determination unit 62B.

The image analysis unit 60B, in the same manner as the image analysis unit 60 of the first embodiment, acquires the first air bubble pattern in the jelly for swallowing captured in the ultrasound image by analyzing the ultrasound image of the jelly for swallowing. In addition, the image analysis unit 60B acquires an optical feature amount of the jelly for swallowing captured in the optical image by analyzing the optical image of the jelly for swallowing captured by the optical camera 5.

The optical feature amount of the jelly for swallowing is not particularly limited and includes at least one of a color of the jelly for swallowing or a second air bubble pattern in the jelly for swallowing. Other optical feature amounts of the jelly for swallowing may be included. The color of the jelly for swallowing may sequentially fade, or the color may sequentially change in accordance with deterioration of the quality. A feature amount acquired as the second air bubble pattern is the same as the first air bubble pattern.

The reference image memory 64B, in the same manner as the reference image memory 64 of the first embodiment, stores a plurality of reference ultrasound images in which the air bubble pattern in the jelly for swallowing in sealing the jelly for swallowing in the package has sequentially changed in accordance with deterioration of the quality of the jelly for swallowing. In addition, the reference image memory 64B stores a plurality of reference optical images in which the optical feature amount of the jelly for swallowing in sealing the jelly for swallowing in the package has sequentially changed in accordance with deterioration of the quality of the jelly for swallowing.

The quality determination unit 62B determines the quality of the jelly for swallowing based on the first air bubble pattern and on the optical feature amount acquired by the image analysis unit 60B. As illustrated in FIG. 8, the quality determination unit 62B includes a first determination unit 70, a second determination unit 71, and a determination result combining unit 72. Each of the first determination unit 70 and the second determination unit 71 is connected to the image analysis unit 60B and to the reference image memory 64B. In addition, the determination result combining unit 72 is connected to the first determination unit 70 and to the second determination unit 71, and the display control unit 33 and the residue detection unit 38 are connected to the determination result combining unit 72.

The first determination unit 70 outputs a first determination result obtained by determining the quality of the jelly for swallowing based on the first air bubble pattern in the jelly for swallowing analyzed by the image analysis unit 60B.

The second determination unit 71 outputs a second determination result obtained by determining the quality of the jelly for swallowing based on the optical feature amount of the jelly for swallowing analyzed by the image analysis unit 60B.

The first determination unit 70 and the second determination unit 71 can also determine the quality of the jelly for swallowing using a machine learning model or well-known various image analysis technologies or the like.

For example, a machine learning model of the first determination unit 70 is the same as the machine learning model of the quality determination unit 62 of the first embodiment.

A machine learning model of the second determination unit 71 is a trained model that uses the optical feature amount of the jelly for swallowing captured in an optical image for learning and the quality of the jelly for swallowing as training data, and that has learned about a relationship between the optical feature amount of the jelly for swallowing captured in the optical image for learning and the quality of the jelly for swallowing for a plurality of pieces of the training data.

The machine learning model takes the optical feature amount of the jelly for swallowing captured in the optical image as an input and outputs an estimation result obtained by estimating the quality of the jelly for swallowing.

The second determination unit 71 determines the quality of the jelly for swallowing based on the estimation result obtained by estimation by the machine learning model.

The determination result combining unit 72 determines the quality of the jelly for swallowing by combining the first determination result of the quality of the jelly for swallowing determined by the first determination unit 70 based on the first air bubble pattern and the second determination result of the quality of the jelly for swallowing determined by the second determination unit 71 based on the optical feature amount. For example, the determination result combining unit 72 determines the quality of the jelly for swallowing by weighting and combining the first determination result and the second determination result.

The quality determination unit 62B may determine the quality of the jelly for swallowing by analyzing both of the ultrasound image and the optical image at once using a multimodal model.

The multimodal model is a trained model that uses the air bubble pattern of the jelly for swallowing captured in the ultrasound image for learning and the optical feature amount of the jelly for swallowing captured in the optical image for learning, and the quality of the jelly for swallowing as training data, and that has learned about a relationship between the air bubble pattern of the jelly for swallowing captured in the ultrasound image for learning and the optical feature amount of the jelly for swallowing captured in the optical image for learning, and the quality of the jelly for swallowing for a plurality of pieces of the training data.

The multimodal model takes the first air bubble pattern of the jelly for swallowing captured in the ultrasound image and the optical feature amount of the jelly for swallowing captured in the optical image as an input and outputs an estimation result obtained by estimating the quality of the jelly for swallowing.

The quality determination unit 62B determines the quality of the jelly for swallowing based on the estimation result obtained by estimation by the multimodal model.

In the ultrasound system of the second embodiment, at least the ultrasound probe 1 (transducer array 11), the image generation unit, the quality determination processing unit 35B including the image analysis unit 60B, the quality determination unit 62B, and the reference image memory 64B, and the optical camera 5 constitute the quality determination system of a jelly for swallowing according to the embodiment of the present invention.

Figure 9:
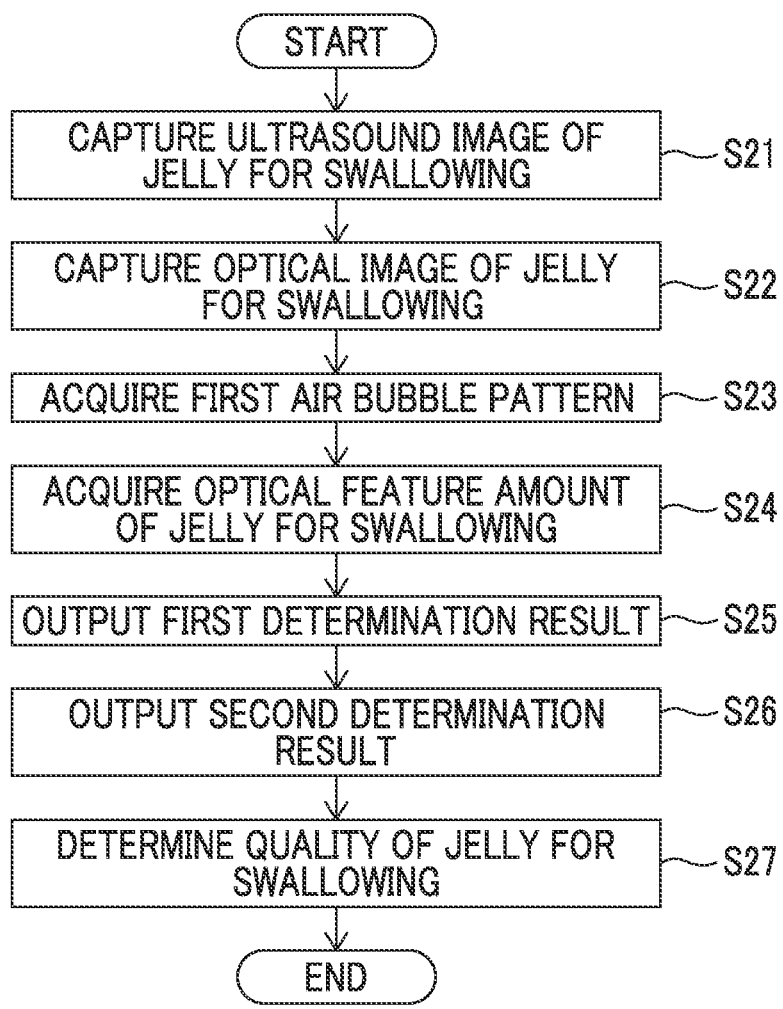
FIG. 9 is a flowchart of one embodiment representing operation of the ultrasound system of the second embodiment in a case of examining dysphagia.

Next, operation of the ultrasound system of the second embodiment in a case of examining dysphagia will be described with reference to the flowchart in FIG. 9.

First, the user captures the ultrasound image of the package of the jelly for swallowing of which the quality is to be determined (step S21).

Next, the user captures the optical image of the same package of the jelly for swallowing (step S22). In this case, the package of the jelly for swallowing is imaged by the optical camera 5, and the optical image of the jelly for swallowing is acquired.

Next, the image analysis unit 60B analyzes the ultrasound image of the jelly for swallowing and acquires the first air bubble pattern in the jelly for swallowing captured in the ultrasound image (step S23). In addition, the image analysis unit 60B analyzes the optical image of the jelly for swallowing and acquires the optical feature amount of the jelly for swallowing captured in the optical image (step S24).

Next, the quality determination unit 62B determines the quality of the jelly for swallowing based on the first air bubble pattern and on the optical feature amount acquired by the image analysis unit 60B.

In this case, the first determination unit 70 determines the quality of the jelly for swallowing based on the first air bubble pattern in the jelly for swallowing captured in the ultrasound image and outputs the first determination result (step S25).

For example, the first determination unit 70 detects a change in the shape of the first air bubble pattern with respect to the air bubble pattern in the jelly for swallowing in sealing the jelly for swallowing in the package and determines the quality of the jelly for swallowing based on the change in the shape of the first air bubble pattern.

A method of detecting the change in the shape of the first air bubble pattern is the same as in the first embodiment.

In addition, the second determination unit 71 determines the quality of the jelly for swallowing based on the optical feature amount of the jelly for swallowing captured in the optical image and outputs the second determination result (step S26).

For example, the second determination unit 71 detects a change in the optical feature amount of the jelly for swallowing with respect to the optical feature amount of the jelly for swallowing in sealing the jelly for swallowing in the package and determines the quality of the jelly for swallowing based on the change in the optical feature amount.

A method of detecting the change in the optical feature amount is not particularly limited. For example, the plurality of reference optical images in which the optical feature amount of the jelly for swallowing in sealing the jelly for swallowing in the package has sequentially changed in accordance with deterioration of the quality of the jelly for swallowing can be stored in the reference image memory 64. The change in the optical feature amount of the jelly for swallowing can be detected by comparing the optical image of the jelly for swallowing with the plurality of reference optical images stored in the reference image memory 64. Accordingly, it is possible to determine the quality of the jelly for swallowing in a plurality of levels based on the change in the optical feature amount of the jelly for swallowing.

Next, the determination result combining unit 72 determines the quality of the jelly for swallowing by combining the first determination result of the quality of the jelly for swallowing determined by the first determination unit 70 and the second determination result of the quality of the jelly for swallowing determined by the second determination unit 71 (step S27).

Subsequent operation is the same as in the first embodiment.

The ultrasound image may be captured after the optical image is captured.

In the ultrasound system of the second embodiment, it is possible to non-invasively determine the quality of the jelly for swallowing based on both of the first air bubble pattern in the jelly for swallowing captured in the ultrasound image and the optical feature amount of the jelly for swallowing. In addition, as in the ultrasound system of the first embodiment, the residue detection unit 38 optimized based on the determination result of the quality of the jelly for swallowing can examine dysphagia of the subject with high accuracy based on the air bubble pattern in the residue of the jelly for swallowing captured in the ultrasound image of the pharynx part of the subject.

In the ultrasound system, a server may be further provided, and a function of at least one of the image analysis unit 60, the quality determination unit 62, or the residue detection unit 38 may be executed in the server.

For example, in a case of executing the function of the residue detection unit 38 in the server, a residue detection unit corresponding to the residue detection unit 38 is provided in the server. The ultrasound image is transmitted to the server from the terminal-side communication circuit 32 of the information terminal 3 through a network. The residue detection unit comprised in the server transmits the presence or absence of the residue, the region of the residue, and the like detected by analyzing the ultrasound image to the terminal-side communication circuit 32 from the server through the network.

Accordingly, even in a case where processing performance of the information terminal 3 is low as in a smartphone or the like, the function of the residue detection unit 38 can be executed using the server having high processing performance. In addition, the function of the residue detection unit comprised in the server can be used from a plurality of ultrasound diagnostic apparatuses. The same applies to a case of executing the function of the image analysis unit 60 or of the quality determination unit 62 in the server.

The present invention is not limited to an ultrasound system of a handheld type and can also be applied to an ultrasound system of a stationary type or to an ultrasound system of a portable type in which an information terminal is constructed of a terminal apparatus of a laptop type. In addition, the image information data generation unit 19 may be comprised in the ultrasound probe 1 or may be comprised in the information terminal 3.

In the apparatus according to the embodiment of the present invention, a hardware configuration of a processing unit that executes various types of processing of the transmission and reception circuit 14, the signal processing unit 16, the image processing unit 17, the probe control unit 21, the display control unit 33, the quality determination processing units 35 and 35B, the residue detection unit 38, the terminal control unit 36, and the like may be dedicated hardware or may be various processors or computers that execute a program. In addition, a hardware configuration of the reference image memories 64 and 64B and the like may be dedicated hardware or may be a memory such as a semiconductor memory or a storage device such as a hard disk drive (HDD) and a solid state drive (SSD).

Examples of the various processors include a central processing unit (CPU) that is a general-purpose processor functioning as various processing units by executing software (program), a programmable logic device (PLD) such as a field programmable gate array (FPGA) that is a processor having a circuit configuration changeable after manufacture, and a dedicated electric circuit such as an application specific integrated circuit (ASIC) that is a processor having a circuit configuration dedicatedly designed to execute specific processing.

One processing unit may be composed of one of the various processors or may be composed of a combination of two or more processors of the same type or different types, for example, a combination of a plurality of FPGAs or a combination of an FPGA and a CPU. In addition, a plurality of processing units may be composed of one of the various processors, or two or more of the plurality of processing units may be collectively configured using one processor.

For example, as represented by a computer such as a server and a client, a form in which one processor is composed of a combination of one or more CPUs and software and the processor functions as the plurality of processing units is possible. In addition, as represented by a system on chip (SoC) and the like, a form of using a processor that implements functions of the entire system including the plurality of processing units in one integrated circuit (IC) chip is possible.

Furthermore, a hardware configuration of the various processors is more specifically an electric circuit (circuitry) in which circuit elements such as semiconductor elements are combined.

In addition, for example, the method according to the embodiment of the present invention can be executed by a program causing a computer to execute each step of the method. In addition, a computer readable recording medium on which the program is recorded can also be provided.

While the present invention has been described in detail so far, the present invention is not limited to the embodiments and may be subjected to various improvements and changes without departing from the gist of the present invention.

EXPLANATION OF REFERENCES

1: ultrasound probe
3: information terminal
5: optical camera
11: transducer array
14: transmission and reception circuit
16: signal processing unit
17: image processing unit
18: probe-side communication circuit
19: image information data generation unit
21: probe control unit
24: battery
25: probe-side processor
32: terminal-side communication circuit
33: display control unit
34: monitor
35, 35B: quality determination processing unit
36: terminal control unit
37: input device
38: residue detection unit
39: terminal-side processor
51: pulser
52: amplification unit
53: AD conversion unit
54: beam former
60, 60B: image analysis unit
62, 62B: quality determination unit
64, 64B: reference image memory
70: first determination unit
71: second determination unit
72: determination result combining unit
80: cup
81: upper lid
82: jelly for swallowing
83: air bubble

What is claimed is:

1. A quality determination system of a jelly for swallowing, the system comprising:
    an ultrasound probe; and
    a processor configured to:

generate an ultrasound image from a reception signal obtained by transmitting and receiving an ultrasound beam to and from a subject using the ultrasound probe;

acquire a first air bubble pattern in a jelly for swallowing by analyzing the ultrasound image generated in a state where the ultrasound probe is in contact with an outer surface of an unopened package in which the jelly for swallowing including air bubbles is sealed; and determine quality of the jelly for swallowing based on the first air bubble pattern.

2. The quality determination system of a jelly for swallowing according to claim 1, wherein the processor detects a change in a shape of the first air bubble pattern with respect to an air bubble pattern in the jelly for swallowing in sealing the jelly for swallowing in the package and determines the quality of the jelly for swallowing based on the change in the shape of the first air bubble pattern.

3. The quality determination system of a jelly for swallowing according to claim 2, the system further comprising:

a memory in which a plurality of reference ultrasound images in which the air bubble pattern has sequentially changed in accordance with deterioration of the quality of the jelly for swallowing are stored, wherein the processor detects the change in the shape of the first air bubble pattern by comparing the ultrasound image with the plurality of reference ultrasound images stored in the memory.

4. The quality determination system of a jelly for swallowing according to claim 1, wherein the processor includes a machine learning model that takes the first air bubble pattern as an input and that outputs an estimation result obtained by estimating the quality of the jelly for swallowing, and determines the quality of the jelly for swallowing based on the estimation result.

5. The quality determination system of a jelly for swallowing according to claim 1, the system further comprising:

an optical camera that acquires an optical image of the unopened package, wherein the processor acquires an optical feature amount of the jelly for swallowing by analyzing the optical image and determines the quality of the jelly for swallowing based on the first air bubble pattern and on the optical feature amount.

6. The quality determination system of a jelly for swallowing according to claim 5, wherein the processor detects a change in a shape of the first air bubble pattern with respect to an air bubble pattern in the jelly for swallowing in sealing the jelly for swallowing in the package, detects a change in the optical feature amount of the jelly for swallowing with respect to the optical feature amount of the jelly for swallowing in sealing the jelly for swallowing in the package, and determines the quality of the jelly for swallowing based on the change in the shape of the first air bubble pattern and on the change in the optical feature amount of the jelly for swallowing.

7. The quality determination system of a jelly for swallowing according to claim 6, the system further comprising:

a memory in which a plurality of reference ultrasound images in which the air bubble pattern has sequentially changed in accordance with deterioration of the quality of the jelly for swallowing, and a plurality of reference optical images in which the optical feature amount of the jelly for swallowing in sealing the jelly for swallowing in the package has sequentially changed in accordance with deterioration of the quality of the jelly for swallowing are stored, wherein the processor detects the change in the shape of the first air bubble pattern by comparing the ultrasound image with the plurality of reference ultrasound images stored in the memory and detects the change in the optical feature amount of the jelly for swallowing by comparing the optical image with the plurality of reference optical images stored in the memory.

8. The quality determination system of a jelly for swallowing according to claim 5, wherein the processor includes a first machine learning model that takes the first air bubble pattern as an input and that outputs a first estimation result obtained by estimating the quality of the jelly for swallowing, and a second machine learning model that takes the optical feature amount of the jelly for swallowing as an input and that outputs a second estimation result obtained by estimating the quality of the jelly for swallowing, and determines the quality of the jelly for swallowing by combining a first determination result obtained by determination based on the first estimation result and a second determination result obtained by determination based on the second estimation result.

9. The quality determination system of a jelly for swallowing according to claim 5, wherein the optical feature amount includes a color of the jelly for swallowing.

10. The quality determination system of a jelly for swallowing according to claim 6, wherein the optical feature amount includes a color of the jelly for swallowing.

11. The quality determination system of a jelly for swallowing according to claim 8, wherein the optical feature amount includes a color of the jelly for swallowing.

12. The quality determination system of a jelly for swallowing according to claim 5, wherein the optical feature amount includes a second air bubble pattern in the jelly for swallowing.

13. The quality determination system of a jelly for swallowing according to claim 8, wherein the optical feature amount includes a second air bubble pattern in the jelly for swallowing.

14. The quality determination system of a jelly for swallowing according to claim 9, wherein the optical feature amount includes a second air bubble pattern in the jelly for swallowing.

15. The quality determination system of a jelly for swallowing according to claim 5, wherein the processor determines the quality of the jelly for swallowing by weighting and combining a first determination result of the quality of the jelly for swallowing determined based on the first air bubble pattern and a second determination result of the quality of the jelly for swallowing determined based on the optical feature amount.

16. The quality determination system of a jelly for swallowing according to claim 10, wherein the processor determines the quality of the jelly for swallowing by weighting and combining a first determination result of the quality of the jelly for swallowing determined based on the first air bubble pattern and a second determination result of the quality of the jelly for swallowing determined based on the optical feature amount.

17. The quality determination system of a jelly for swallowing according to claim 5,
wherein the processor includes a multimodal model that takes the first air bubble pattern and the optical feature amount as an input and that outputs an estimation result obtained by estimating the quality of the jelly for swallowing, and determines the quality of the jelly for swallowing based on the estimation result.

18. The quality determination system of a jelly for swallowing according to claim 1,
wherein the processor includes a machine learning model that takes the ultrasound image generated in a state where the ultrasound probe is in contact with a pharynx part of the subject who has swallowed the jelly for swallowing as an input and that outputs an estimation result obtained by estimating at least one of presence or absence of the residue or a region of the residue, acquires an air bubble pattern in a residue of the jelly for swallowing by analyzing the ultrasound image, and optimizes the machine learning model based on a determination result of the quality of the jelly for swallowing.

19. The quality determination system of a jelly for swallowing according to claim 13, the system further comprising:
an ultrasound diagnostic apparatus including the ultrasound probe; and
a server connected to the ultrasound diagnostic apparatus through a network,
wherein the processor includes:
a first processor disposed in the ultrasound diagnostic apparatus; and
a second processor disposed in the server,
the first processor generates the ultrasound image from the reception signal obtained by transmitting and receiving an ultrasound beam to and from the subject using the ultrasound probe, and
the second processor performs at least one of (A) to (C):
(A) acquiring the first air bubble pattern in the jelly for swallowing by analyzing the ultrasound image generated in a state where the ultrasound probe is in contact with the outer surface of the unopened package in which the jelly for swallowing including air bubbles is sealed;
(B) determining quality of the jelly for swallowing based on the first air bubble pattern;
(C) acquiring an air bubble pattern in a residue of the jelly for swallowing by analyzing the ultrasound image generated in a state where the ultrasound probe is in contact with a pharynx part of the subject who has swallowed the jelly for swallowing, and detecting at least one of presence or absence of the residue or a region of the residue based on the air bubble pattern in the residue.

20. A quality determination method of a jelly for swallowing, the method comprising:
generating an ultrasound image from a reception signal obtained by transmitting and receiving an ultrasound beam in a state where an ultrasound probe is in contact with an outer surface of an unopened package in which a jelly for swallowing including air bubbles is sealed;
acquiring a first air bubble pattern in the jelly for swallowing by analyzing the ultrasound image; and
determining quality of the jelly for swallowing based on the first air bubble pattern.

* * * * *